United States Patent [19]

Ueda et al.

[11] Patent Number: 4,657,901

[45] Date of Patent: Apr. 14, 1987

[54] PHARMACEUTICAL COMPOSITION

[75] Inventors: Haruhiko Ueda, Yokohama; Hidekazu Toyoda, Urawa; Minoru Fukuda, Sagamihara, all of Japan

[73] Assignees: Sheiseido Company, Ltd., Tokyo; Takeda Chemical Industries, Ltd., Osaka, both of Japan

[21] Appl. No.: 648,276

[22] Filed: Sep. 7, 1984

[30] Foreign Application Priority Data

Sep. 7, 1983 [JP] Japan ................................ 58-164356
Jul. 27, 1984 [JP] Japan ................................ 59-157009

[51] Int. Cl.⁴ .............................................. A61K 31/56
[52] U.S. Cl. ...................................... 514/171; 514/859
[58] Field of Search ......................... 514/171; 424/81; 260/397.4

[56] References Cited

U.S. PATENT DOCUMENTS 3,856,829 12/1974 Hiraga et al. ..................... 260/397.4
4,514,385 4/1985 Damani et al. ........................ 424/81

OTHER PUBLICATIONS

Chem. Abstracts vol. 98 (26) Par 221834(a).

Primary Examiner—Leonard Schenkman
Assistant Examiner—Joseph A. Lipovsky
Attorney, Agent, or Firm—Wenderoth, Lind & Ponack

[57] ABSTRACT

The present invention concerns a composition for topical application which is greatly useful for the treatment of acne. The composition contains (1) a compound of the formula:

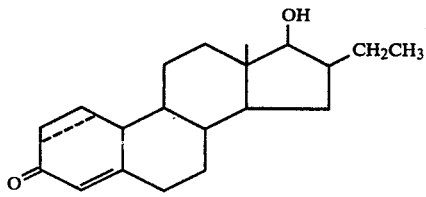

or its ester or ether, (2) keratolytic agent and (3) pharmaceutically acceptable carrier.

18 Claims, No Drawings

PHARMACEUTICAL COMPOSITION

This invention relates to a preparation for topical application intended for the treatment of acne.

Acne is common inflammatory disease of sebaceous glands that occurs so frequently during adolescence, being more specifically named acne vulgaris, and is clinically defined as "a chronic inflammatory lesion occurring in the hair follicle, principally in the pilosebaceous gland system". Acne, of which the mechanism has not yet been satisfactory established at present, is a skin disease caused by different complicated factors, whereby excessive excretion of sebum, cornification of the hair follicle and bacteria in the hair follicle are generally considered to play an important role in causing acne. As the topical medication for the treatment of acne, therefore, frequent use has been normally made of the creams or ointments having the sebum excretion depressant, and antimicrobial substances incorporated into them. However, none of the commercially available preparations for the treatment of acne are completely free from a wide variety of defects. For example, hormones of the female type, which act as a sebum excretion depressant, suppress the growth of the epidermis and reduce excretion of the sebaceous gland, but the side-effects (e.g. estrogenic effect) brought about by the hormone of the female type are not desirable to males and females at puberty; and, the antimicrobial agents, such as hexachlorophene, trichlorocarbanilide and benzalkonium chloride, demonstrate in vitro exceedingly high antimicrobial activity against *Propionibacterium acnes*, an acne bacterium ordinarily found on the skin, but when being in practice incorporated into creams, ointments, etc. and used for the treatment of acne, mostly fail to produce the expected therapeutic effect.

The present inventors, after intensive research to obtain a pharmaceutical preparation being free from the side-effects, being mild to the skin and being superior in therapeutic effect against acne, found that a composition which contains (1) a compound of the formula:

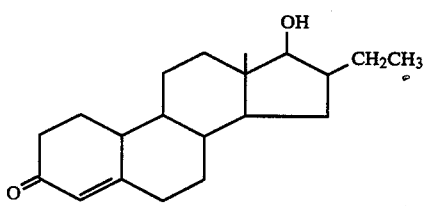

wherein the dotted line at 9(10) position indicates a saturated bond or an unsaturated double bond, or its ester or ether (hereinafter referred to briefly as "Compound [I]"), (2) keratolytic agent and (3) pharmaceutically acceptable carrier, attains an unexpectedly enhanced therapeutic effect through the combination effect of the Compound [I] and the keratolytic agent. Furthermore, the present inventors have also unexpectedly found that a composition comprising Compound [I], keratolytic agent, gelling agent and alcohol shows further enhancement of the therapeutic effect in a shorter period in the treatment of acne through the increased adsorption of the Compound [I] into the lesion. The present invention is a culmination of these unexpected findings.

The Compound [I] which is used in the present invention possesses excellent inhibitory activity against hormones of the male type [the U.S. Pat. Specification No. 3856829, the Japanese Unexamined Patent Publication No. 53499/1982 and the Japanese Patent Application No. 57227/1983]. The dotted line at 9(10) position of Compound [I] indicates a saturated bond or an unsaturated double bond. Therefore, Compound [I] consists of the following two compounds (Ia and Ib) and their esters and ethers.

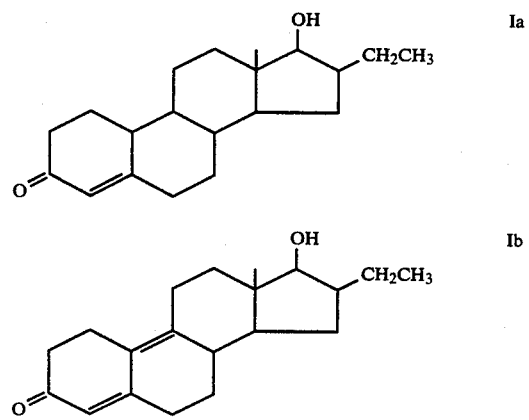

The Compound [Ia] is oxedolone (16 β-ethyl-17 β-hydroxy-4-estren-3-on) and has been put on the market as a therapeutic agent for prostatomegaly (Tradename of "Prostetin", produced by Takeda Chemical Industries, Ltd., in Japan).

The esters and ethers which are included in the Compound [I] mean the compounds of [I] where the hydroxy portion at the 17-position is esterified and etherified, respectively. As the ester at the 17-position, there may be mentioned esters with $C_{1-18}$ alkanoyl groups and $C_{2-18}$ alkenoyl groups, wherein these groups may be substituted. Specific examples of the $C_{1-18}$ alkanoyl groups include formyl, acetyl, propionyl, butyryl, isobutyryl, valeryl, pivaloyl, caproyl, enanthoyl, capryloyl, lauroyl, myristoyl, palmitoyl, stearoyl, etc. Specific examples of the $C_{2-18}$ alkenoyl groups include crotonoyl, oleoyl, linoleoyl, linolenoyl, etc. As the substituents on these alkanoyl and alkenoyl groups, there may be mentioned halogen atoms (e.g. fluorine, chlorine, etc.), hydroxyl group, mercapto group, oxo group, thioxo group, $C_{1-6}$ alkoxy groups (e.g., methoxy, ethoxy, etc.), $C_{1-6}$ alkylthio groups (e.g., methylthio, ethylthio, etc.), $C_{1-18}$ alkanoyloxy groups ($C_{1-18}$ alkanoyls include for example those as mentioned above), $C_{2-18}$ alkenoyloxy groups (alkenoyls include for example those as mentioned above), $C_{6-12}$ aryl groups (e.g., phenyl, naphthyl, etc.), $C_{6-12}$ aryloxy groups (e.g., phenoxy, naphthyloxy, etc.), and so forth. Among more specific examples of the substituted alkanoyl groups are chloroacetyl, phenylacetyl, phenoxyacetyl, benzoyl, caproyloxyacetyl, enanthoyloxyacetyl, (2-ethylbutyryloxy)acetyl, etc. As the ether at the 17-position, there may be mentioned ethers with $C_{1-6}$ alkyl groups such as methyl, ethyl, propyl, butyl and pentyl, and ethers with $C_{1-6}$ alkoxy-$C_{1-6}$ alkyl groups such as methoxymethyl, methoxyethyl, ethoxymethyl and ethoxyethyl as well as ethers with groups such as tetrahydropyranyl, tetrahydrofuryl and tetrahydrothienyl. The above-mentioned esters and ethers are easily produced by the known method or a per se known method.

The amount of the Compound [I] to be incorporated into the composition of the present invention is at a ratio of about 0.001 to about 2 W/V %.

The keratolytic agent which is used in the present invention denotes a compound which exhibits the action of suppressing the hypercornification of ducts of the sebaceous gland, and specifically includes sulfur, selenium disulfide, urea, benzoyl peroxide, resorcinol, salicylic acid, vitamin A acid, etc., with preferable examples being urea and resorcinol.

The amount of the keratolytic agent to be incorporated into the composition of the present invention is at a ratio of about 0.001 to about 15 W/V %, and preferably is about 1.0 to about 15 W/V % in the case of sulfur, selenium disulfide and benzoyl peroxide, about 0.005 to about 0.1 W/V % in the case of vitamin A acid and about 0.05 to about 5 W/V % in the case of other keratolytic agents.

As the pharmaceutically acceptable carrier which is used in the present invention, there may be mentioned gelling agents, alcohols, sebum excretion depressants, antimicrobial agents, surface active agents, thickening agents, humidifying agents, astringents, pH adjusting agents, perfumes, colorants, water, etc. The carrier can be incorporated into the preparation for topical application according to the present invention to such an extent as may not impair the effect of the preparation. Among others, a gelling agent and/or an alcohol are preferably used as carriers. A gelling agent and an alcohol improves poor solubility being so far regarded as the defect of the Compound [I] from the standpoint of processing it into preparations.

As the gelling agent which is used in the present invention, specifically, there may be mentioned carboxyvinyl polymers (hereinafter abbreviated as CVP, with the average molecular weight of 10 millions to 500 millions, preferably, 100 millions to 300 millions, such as Carbopol® 940 and 941, produced by Goodrich Chemical Co., in U.S.A., Hivis Wako® 103, 104 and 105 produced by Wako Pure Chemical Industries, Ltd., in Japan, and so forth), carboxymethylcellulose, sodium carboxymethylcellulose, methylcellulose, hydroxyethylcellulose hydroxypropylcellulose, polyvinyl alcohol (with a degree of polymerization of about 500 to about 2000), etc., with the preferred example being CVP. These gelling agents exhibit gelling action and in some instances act as a thickening agent and stabilizer, as well.

The amount of the gelling agent to be incorporated into the composition of the present invention is generally at a ratio of about 0.001 to about 20 W/V %. For CVP mentioned above as the preferred example, the preferable amount incorporated is about 0.01 to about 5 W/V %.

As the alcohols which are used in the present invention, there may be mentioned monohydric alcohols and polyhydric alcohols, and the above-mentioned alcohols may be used singly or in combination. Examples of the monohydric alcohols include aliphatic $C_{1-18}$ alcohols such as ethanol, n-propanol, i-propanol, n-butanol, i-butanol, sec-butanol, tert-butanol, n-pentanol, n-hexanol, lauryl alcohol and cetyl alcohol; alicyclic $C_{3-7}$ alcohols such as cyclopropanol and cyclobutanol; and phenyl-$C_{1-6}$ alkanols such as benzyl alcohol and phenetyl alcohol. Among others, ethanol and benzyl alcohol are frequently used, and these alcohols, making up for low solubility of the Compound [I], function to increase absorption and penetration of the composition of the present invention. As examples of the polyhydric alcohols, there may be mentioned aliphatic $C_{2-6}$ polyhydric alcohols (with a number of hydroxyl groups of 2 to 6), such as ethylene glycol, propylene glycol, trimethylene glycol, 1,3-butanediol, glycerol and sorbitol, as well as diethylene glycol, polyethylene glycols (with an average molecular weight of 200 to 2000), dipropylene glycol, polypropylene glycols (with an average molecular weight of 200 to 2000), and so forth. Like the monohydric alcohols, these polyhydric alcohols act as a solvent, and in some instances function as a humidifying agent.

The amount of the alcohols to be incorporated into the composition of the present invention is at a ratio of about 5 to about 70 W/V %.

As the sebum secretion depressant, there may be mentioned hormones of the female type such as estradiol. Examples of the antimicrobial agents include hexachlorophene, trichlorocarbanilide, benzalkonium chloride, phenol, cetyl pyridinium chloride, undecylenic acid and bithionol. As the surface active agent, there may be mentioned nonionic surface active agents, anionic surface active agents, amphoteric surface active agents, etc., and the preferred examples are nonionic surface active agents and anionic surface active agents. Examples of the nonionic surface active agents include polyoxyethylene aliphatic alcohol ethers (with a degree of ethylene oxide polymerization of 5 to 50, in which the aliphatic alcohol residues have 12 to 18 carbon atoms; for example Brij® 35, 78 and 98, etc., produced by Kao Atlas Co., in Japan; hereinafter "ethyleneoxide" is abbreviated as "EO"), polyoxyethylene fatty acid esters (with a degree of EO polymerization of 8 to 50, in which the fatty acid residues have 12 to 18 carbon atoms; for example Myrj® 45, 52 and 53, etc., produced by Kao Atlas Co., in Japan), fatty acid esters of sorbitan (with a degree of EO polymerization of 0 to 40, in which the fatty acid residues have 12 to 18 carbon atoms; for example Tween® 20, 40, 60 and 80, Span® 20, 40, 60 and 80, etc., produced by Kao Atlas Co., in Japan), polyoxyethylene hydrogenated castor oils (with a degree of EO polymerization of 5 to 60, for example Nikkol® HCO-50, HCO-60 and HCO-100, etc., produced by Nikko Chemicals Co., Ltd., in Japan), and so forth. In the above nonionic surface active agents, examples of $C_{12-18}$ aliphatic alcohol residues are lauryl, cetyl and so forth and examples of $C_{12-18}$ fatty acid residues are lauroyl, palmitoyl, stearoyl and so forth. As examples of the anionic surface active agents, there may be mentioned sodium soaps (having 12 to 18 carbon atoms, for example sodium lauroate, sodium stearoate), potassium soaps (having 12 to 18 carbon atoms, for example potassium lauroate, potassium stearate), etc. Examples of the astringents include tannin and so forth. Examples of the humidifying agents include hyaluronic acid, sodium hyaluronate, chondroitin sulfate, pyrrolidonecarboxylic acid, sodium pyrrolidonecarboxylate and so forth. As the pH adjusting agent, there may be mentioned acids and bases which are usually employed in this field. Thus, examples of acids used as the pH adjusting agent are hydrochloric acid, citric acid, etc. and examples of bases used as the pH adjusting agent are sodium hydroxide, potassium hydroxide, triethanolamine, diisopropanolamine, etc.

The composition of the present invention can be prepared by mixing, by a per se known method, (1) the Compound [I], (2) keratolytic agent and (3) pharmaceutically acceptable carrier.

As the pH value of the composition of the present invention is normally within the range of 4 to 8 and preferably 6 to 8, pH adjusting agents as described above can be used to adjust the pH value.

The most preferable composition comprises oxendolone, a keratolytic agent (urea or resorcinol), carboxyvinyl polymer, ethyl alcohol and benzyl alcohol. This composition may contain further additional carrier(s) as mentioned above. The composition which comprises oxendolone, a keratolytic agent (urea or resorcinol), carboxyvinyl polymer, ethyl alcohol and benzyl alcohol shows especially high therapeutic effect to acne and causes no irritation to the skin.

The properties of the preparation for topical application according to the present invention may be those of any kind being applicable to the external skin, such as cream, ointment and lotion. Methods for producing cream, ointment, lotion and other type of preparations for topical use are per se known and well established in the pharmaceutical field. Also in the present invention, such known technique can be applied to producing the composition of the present invention in the form of cream, ointment, lotion, etc. The formulation examples for ointment are described in the Example.

Action

The preparation for topical application according to the present invention may be applied to the affected part normally once to several times daily in the single dose within the range of 0.1 mg to 0.5 g, depending upon its symptoms. This method normally permits mild acne to clear up within several days and even severe acne to disappear in two to three weeks. In addition, the present therapy can be applied without any side-effects observed.

EXAMPLE

Gel ointments containing 0.2 to 2.0 W/V % of exendolone were prepared as the following Examples and Table.

Formulation Example 1

In a mixed solution consisting of 5.0 g of benzyl alcohol and 20.0 g of ethanol was dissolved 0.2 g of oxendolone, and 15.0 g of polyethylene glycol (PEG-600) was added, for dissolution, to the solution, followed by the addition of a solution of 1.0 g of urea in 10.0 g of purified water. Then, a solution of 0.8 g of a carboxyvinyl polymer (Carbopol 940) and 0.1 g of hyaluronic acid in 20.0 g of purified water was added, and after stirring and mixing, 27.7 g of purified water was added, followed by the neutralization with 0.2 g of triethanolamine to produce a gel-like ointment for topical application.

Formulation Examples 2 and 3

Gel-like ointments containing the same ingredients as in Example 1 were produced in the similar manner to Example 1.

Formulation Examples 4 to 8

In a mixed solution of benzyl alcohol and ethanol further containing or not containing 1,3-butanediol was dissolved oxendolone, and polyethylene glycol (PEG-300) was added, for dissolution, to the solution, followed by the addition of a solution of a keratolytic agent (urea, resorcinol or benzoyl peroxide) or mixture of keratolytic agents in a part of purified water. Then, a solution of a carboxyvinyl polymer and polyoxyethylene hydrogenated castor oil (further containing or not containing hydroxypropylcellulose or polyvinyl alcohol) and hyaluronic acid in purified water was added, and after stirring and mixing rest of water was added, followed by the neutralization with diisopropanolamine.

TABLE

Formulation Examples

Unit: g

| Ingredient | 1 | 2 | 3 | 4 | 5 | 6 | 7 | 8 |
|---|---|---|---|---|---|---|---|---|
| Oxendolone | 0.2 | 0.5 | 0.2 | 2.0 | 1.5 | 1.0 | 0.2 | 2.0 |
| Benzyl alcohol | 5.0 | 10.0 | 5.0 | 10.0 | 5.0 | 10.0 | 5.0 | 10.0 |
| Ethanol | 20.0 | 25.0 | 20.0 | 37.0 | 35.0 | 30.0 | 40.0 | 37.0 |
| Polyethylene glycol PEG-300 | | | | 10.0 | | 10.0 | | 10.0 |
| Polyethylene glycol PEG-600 | 15.0 | 20.0 | 15.0 | | | | | |
| 1,3-Butanediol | | | | | 20.0 | 5.0 | 20.0 | |
| Carboxyvinyl polymer Carbopol 940 | 0.8 | 0.6 | 0.2 | 1.0 | 0.8 | 1.0 | 0.8 | 1.0 |
| Hydroxypropylcellulose | | | | | 0.2 | | 0.2 | |
| Polyvinyl alcohol | | | | 0.1 | | | | 0.1 |
| Hyaluronic acid | 0.1 | 0.1 | 0.2 | | | | | |
| Polyoxyethylene hydrogenated castor oil, Nikkol HCO-60 | | | | 2.0 | 2.0 | 2.0 | 2.0 | 2.0 |
| Urea | 1.0 | 1.0 | 3.0 | 1.0 | | | | 1.0 |
| Resorcinol | | | | | 2.0 | | | 1.0 |
| Salicylic acid | | | | | | 0.5 | | |
| Benzoyl peroxide | | | | | | | 15.0 | |
| Triethanolamine | 0.2 | 0.2 | 0.1 | | | | | |
| Diisopropanolamine | | | | 0.2 | 0.2 | 0.2 | 0.2 | 0.2 |
| Purified water | 57.7 | 42.6 | 56.3 | 36.7 | 33.3 | 40.3 | 16.6 | 35.7 |

Clinical test:

The clinical tests are described in the following to illustrate the phramaceutical effects of the present invention in more detail.

Medicament preparation used

The gel ointment-type preparation for topical application as produced in the Formulation Example 1 was used.

Patients applied with the preparation and duration of observation.

15 to 30 year old, males and females to a total of 15 patients.

Method of application

After the patients thoroughly washed their faces with use of toilet soap, the above mentioned ointment-type preparation was applied for topical application only onto the efflorescence once to three times a day.

Items of observation and duration of observation

The patients were observed for three symptoms, i.e., comedo, papule and pustule, and the severity of each symptom observed was rated on a scale divided into five grades of intense (4), moderate (3), slight (2), little (1) and none (0). By putting the severities of these three symptoms together, the degree of before-treatment seriousness of acne vulgaris was divided into three grades of severe, mild and minor acne. The observations for progress were made at the times of before treatment(O) and one week (I), two weeks (II), three weeks (III), and four weeks (IV) after treatment.

Degree of overall improvement

The degree of improvement in symptoms brought about by the medicament preparation used over the before-treatment symptoms was divided into five grades of marked relief (+++), fair relief (++), slight relief (+), no relief (±) and aggravation (−).

Usefulness

On the basis of the degree of overall improvement, the effect of the medicament preparation used was rated as greatly useful (+++), fairly useful (++), slightly useful (+) and useless (±).

| Case No. | Age | Sex | Serious-ness | Comedo | | | | | Papule | | | | | Pustule | | | | | | DOI* | | | Useful-ness |
|---|---|---|---|---|---|---|---|---|---|---|---|---|---|---|---|---|---|---|---|---|---|---|---|
| | | | | 0 | I | II | III | IV | 0 | I | II | III | IV | 0 | I | II | III | IV | I | II | III | IV | |
| 1 | 16 | Female | Mild | 2 | 2 | 2 | 2 | 2 | 2 | 2 | 2 | 1 | 2 | 1 | 1 | 1 | 1 | 1 | ± | ± | ± | ± | ± |
| 2 | 20 | Male | " | 3 | 2 | 2 | 1 | 0 | 2 | 1 | 0 | 0 | 0 | 1 | 1 | 0 | 0 | 0 | ++ | ++ | +++ | +++ | +++ |
| 3 | 30 | Female | " | 2 | 2 | 2 | 1 | 0 | 2 | 2 | 1 | 1 | 1 | 2 | 2 | 1 | 1 | 1 | ± | + | ++ | ++ | ++ |
| 4 | 21 | " | Severe | 4 | 4 | 3 | 2 | 1 | 4 | 3 | 3 | 2 | 1 | 3 | 2 | 2 | 1 | 0 | + | ++ | +++ | +++ | +++ |
| 5 | 25 | " | " | 4 | 4 | 4 | 3 | 2 | 3 | 3 | 2 | 1 | 1 | 3 | 3 | 2 | 1 | 0 | ± | + | ++ | +++ | ++ |
| 6 | 24 | Male | Mild | 3 | 1 | 1 | 0 | 0 | 3 | 2 | 2 | 1 | 0 | 3 | 2 | 1 | 1 | 0 | ++ | +++ | +++ | +++ | +++ |
| 7 | 26 | Female | " | 3 | 3 | 2 | 2 | 2 | 2 | 1 | 2 | 1 | 1 | 2 | 1 | 1 | 1 | 1 | + | ± | + | + | + |
| 8 | 19 | " | Severe | 3 | 2 | 1 | 0 | 0 | 4 | 3 | 2 | 2 | 1 | 3 | 1 | 0 | 0 | 0 | ++ | +++ | +++ | +++ | +++ |
| 9 | 15 | " | Mild | 3 | 2 | 1 | 0 | 0 | 3 | 1 | 1 | 0 | 0 | 3 | 2 | 1 | 0 | 0 | ++ | +++ | +++ | +++ | +++ |
| 10 | 23 | " | " | 1 | 0 | 0 | 0 | 0 | 3 | 3 | 1 | 0 | 0 | 3 | 1 | 0 | 0 | 0 | ++ | +++ | +++ | +++ | +++ |
| 11 | 20 | " | " | 1 | 0 | 0 | 0 | 0 | 2 | 1 | 0 | 0 | 0 | 1 | 0 | 0 | 0 | 0 | ++ | +++ | +++ | +++ | +++ |
| 12 | 18 | Male | Severe | 3 | 2 | 1 | 0 | 0 | 4 | 2 | 1 | 1 | 0 | 2 | 0 | 0 | 0 | 0 | ++ | +++ | +++ | +++ | +++ |
| 13 | 24 | Female | Mild | 3 | 2 | 2 | 1 | 1 | 3 | 3 | 1 | 0 | 0 | 1 | 0 | 0 | 0 | 0 | + | ++ | +++ | +++ | ++ |
| 14 | 20 | " | " | 3 | 1 | 1 | 1 | 1 | 3 | 1 | 1 | 1 | 1 | 1 | 1 | 0 | 0 | 0 | ++ | ++ | ++ | ++ | ++ |
| 15 | 27 | " | " | 2 | 1 | 0 | 0 | 0 | 3 | 2 | 1 | 0 | 0 | 0 | 0 | 0 | 0 | 0 | ++ | ++ | +++ | +++ | +++ |

Note: *the degree of overall improvement.

As being clear from the above results, the clinical test results on these 15 cases consisting of 3 males and 12 females, in which ± (useless) accounted for 1 case (7%), +(slightly useful) 1 case (7%), ++ (fairly useful) 4 cases (26%) and +++ (greatly useful) 9 cases (60%), demonstrate the good effect produced by the preparation for topical application according to the present invention.

What we claim is:

1. A composition for the topical treatment of acne, which comprises
   (1) an effective amount for treating acne of oxendolone or its ester or ether, (2) a keratolytic agent, and (3) a pharmaceutically acceptable carrier.

2. The composition according to claim 1, wherein the content of oxendolone is from about 0.001 W/V % to about 2 W/V % relative to the whole composition.

3. The composition according to claim 1, wherein the keratolytic agent is urea.

4. The composition according to claim 1, wherein the keratolytic agent is resorcinol.

5. The composition according to claim 1 wherein the oxendolone is from about 0.001 W/V % to about 2 W/V % relative to the whole composition and the keratolytic agent is present in an amount of 0.001 to about 15 W/V %.

6. The composition according to claim 1 which contains a gelling agent in an amount of 0.001 to about 20 W/V % and an alcohol in an amount of 5 to 70 W/V %.

7. The composition according to claim 1, wherein the composition comprises a gelling agent and/or an alcohol.

8. The composition according to claim 7, wherein the gelling agent is carboxyvinyl polymer.

9. The composition according to claim 7, wherein the alcohol is ethyl alcohol.

10. The composition according to claim 7, wherein the alcohol is benzyl alcohol.

11. The composition according to claim 7, which comprises oxendolone, urea, carboxyvinyl polymer, ethyl alcohol and benzyl alcohol.

12. The composition according to claim 7, which comprises oxendolone, resorcinol, carboxyvinyl polymer, ethyl alcohol and benzyl alcohol.

13. The composition according to claim 7, wherein the content of the oxendolone is from about 0.001 W/V % to about 2 W/V % relative to the whole composition.

14. The composition according to claim 7, wherein the keratolytic agent is urea.

15. The composition according to claim 7, wherein the heratolytic agent is resorcinol.

16. A method of treatment of acne which comprises administering topically the composition containing
   (1) an effective amount for treating acne of oxendolone, or its ester or ether,
   (2) a keratolytic agent, and
   (3) a pharmaceutically acceptable carrier.

17. A method according to claim 16 wherein the oxendolone is present in an amount of from about 0.001 W/V % to about 2 W/V % relative to the whole composition and the keratolytic agent is present in an amount of 0.001 to about 15 W/V %.

18. A method according to claim 17 which contains a gelling agent in an amount of 0.001 to about 20 W/V % and an alcohol in an amount of 5 to 70 W/V %.

* * * * *